(12) United States Patent
Shami (10) Patent No.: US 10,994,156 B2
(45) Date of Patent: May 4, 2021

(54) HAIR DYE AND METHODS OF USING THE SAME

(71) Applicant: FAROUK SYSTEMS, INC., Houston, TX (US)

(72) Inventor: Farouk M. Shami, Houston, TX (US)

(73) Assignee: Farouk Systems, Inc., Houston, TX (US)

( * ) Notice: Subject to any disclaimer, the term of this patent is extended or adjusted under 35 U.S.C. 154(b) by 0 days.

(21) Appl. No.: 16/486,474

(22) PCT Filed: Feb. 23, 2018

(86) PCT No.: PCT/US2018/019430
§ 371 (c)(1),
(2) Date: Aug. 15, 2019

(87) PCT Pub. No.: WO2018/156900
PCT Pub. Date: Aug. 30, 2018

(65) Prior Publication Data
US 2020/0230442 A1     Jul. 23, 2020

Related U.S. Application Data

(60) Provisional application No. 62/463,785, filed on Feb. 27, 2017.

(51) Int. Cl.
*A61Q 5/10* (2006.01)
*A45D 7/06* (2006.01)
(Continued)

(52) U.S. Cl.
CPC .................. *A61Q 5/10* (2013.01); *A45D 7/06* (2013.01); *A61K 8/72* (2013.01); *A61Q 5/065* (2013.01);
(Continued)

(58) Field of Classification Search
CPC .. A61Q 5/10; A61K 2800/87; A61K 2800/43; A61K 2800/81; A61K 8/77;
(Continued)

(56) References Cited

U.S. PATENT DOCUMENTS

| | | |
|---|---|---|
| 3,617,165 A | 11/1971 | Kalopissis |
| 2007/0245502 A1 | 10/2007 | Ghannad |
| 2015/0173480 A1* | 6/2015 | Washington ........... A45D 2/367 |
| | | 132/206 |

FOREIGN PATENT DOCUMENTS

| | | |
|---|---|---|
| WO | 2007127065 A2 | 11/2007 |
| WO | WO 2007/127065 A2 * | 11/2007 |
| WO | 2008009579 A1 | 1/2008 |

OTHER PUBLICATIONS

PCT Search Report recieved in co-pending PCT Application No. PCT/US18/19430, dated May 3, 2018, 9 pages.

* cited by examiner

*Primary Examiner* — Eisa B Elhilo
(74) *Attorney, Agent, or Firm* — Blank Rome LLP (57) ABSTRACT

A method of hair dying is provides that includes applying a polymer based hair dye to hair and emitting light on the applied polymer based hair dye for a duration to cure the polymer based hair dye on the hair. In certain aspects a device is provided that emits polymer curative energy for curing an applied polymer based hair dye that includes a housing, at least polymer curative light source disposed in the housing, and a controller operatively connected to the heat source and the at least one polymer curative light source. In certain embodiments a heat source is disposed in the housing that includes a polymer curative light source.

19 Claims, 3 Drawing Sheets

(51) Int. Cl.
*A61K 8/72* (2006.01)
*A61Q 5/06* (2006.01)
*A45D 7/00* (2006.01)
*A45D 19/00* (2006.01)

(52) U.S. Cl.
CPC .... *A45D 19/0066* (2021.01); *A45D 2007/001* (2013.01); *A45D 2200/205* (2013.01); *A61K 2800/43* (2013.01); *A61K 2800/81* (2013.01); *A61K 2800/87* (2013.01)

(58) Field of Classification Search
CPC ...... A45D 2200/205; A45D 2019/0066; A45D 2200/057; A45D 2007/001
USPC .......................................................... 8/405
See application file for complete search history.

HAIR DYE AND METHODS OF USING THE SAME

REFERENCE TO RELATED APPLICATIONS

This application is a national stage of International Patent Application No. PCT/US2018/019430 filed Feb. 23, 2018, which claims the benefit of U.S. Provisional Application Ser. No. 62/463,785 filed Feb. 27, 2017, the contents of which are incorporated herein by reference in their entirety.

FIELD OF THE INVENTION

This invention relates generally to hair dying compositions and methods.

BACKGROUND OF THE INVENTION

Without limiting the scope of the invention, its background is described in connection with existing methods and compositions for dying hair.

Currently, hair may be dyed by selecting a premixed hair dye, such a hair dye provided by retail sources (e.g., through an oxidation system or with direct dyes). When a user wants a particular hair color that is not provided premixed and ready to apply, the user may work with a stylist to achieve the particular hair color. The stylist may manually mix different dye ingredients to develop a dye color that may achieve the particular hair color. In some cases, a machine may be used to mix the different dye ingredients.

In direct dye applications, hair dye may be mixed by combining various amounts of colorants having three primary colors (blue, red and yellow). Other dye ingredients may include, for example, an oxidizing liquid, developers, emulsifiers, stabilizers and surfactants.

"Permanent" hair dye (where dyed color may begin to fade, for example, in about 4 to 6 weeks) may include two compositions, including an oxidizing agent such as hydrogen peroxide and a hair dye or dye precursor, that are mixed immediately prior to application to hair. Dye precursors in the mixed composition may be able to penetrate into the hair shaft. During a development time, the dye precursors may oxidize and color the interior of the hair shaft. After the development time, the mixed composition may be rinsed from the hair, leaving the dyed hair permanently altered. "Semi-permanent" hair dye may include preformed dye molecules (premixed compositions), and may wash out of the hair, for example, after about 6 to 12 shampooings.

SUMMARY OF THE INVENTION

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments of the present disclosure relate to a method that includes applying a polymer based hair dye to hair, and emitting polymer curative energy such as ultraviolet light (UV) onto the applied polymer based hair dye at a UV wavelength and for a duration sufficient to cure the polymer based hair dye on the hair. The polymer based hair dye may be applied by methods including but not limited to applying to hair with a mister and brushing the polymer based hair dye into the hair.

In certain embodiments the polymer curative energy is emitted from a hair device. In particular embodiments, the polymer curative energy is applied by passing a hair iron around sections of the hair, where the polymer curative energy is emitted from the hair iron. In certain embodiments, the hair iron includes a heat source and heat transferable plates that apply heat to hair and at least one polymer curative energy source that applies polymer curative energy to the hair. The application of heat and polymer curative energy is simultaneous in certain embodiments and sequential in others. In certain embodiments involving a polymer curative light such as for example a polymer curative ultraviolet light, the polymer curative light may be applied by performing multiple passes of the hair device to direct the polymer curative light on the polymer based hair dye over sections of the hair at a time.

In another aspect, embodiments of the present disclosure relate to a method that includes curing a polymer based hair dye on hair, wherein the polymer based hair dye comprises colorants, an initiator, and at least one of a polymerizable oligomer, a polymerizable monomer, and combinations of polymerizable oligomers and monomers.

In yet another aspect, embodiments of the present disclosure relate to a hair device that includes a housing, a heat source disposed in the housing, at least one polymer curative energy source such as an ultraviolet light source disposed in the housing, and a controller operatively connected to the heat source and the at least one polymer curative energy source. The polymer curative light source in certain embodiments is light source that generates a sufficient amount of light in the ultraviolet (UV) frequencies to induce polymerization of the polymer in the polymer based hair dye.

Other aspects and advantages of the invention will be apparent from the following description and the appended claims.

BRIEF DESCRIPTION OF THE DRAWINGS

For a more complete understanding of the present invention, including features and advantages, reference is now made to the detailed description of the invention along with the accompanying figures.

DETAILED DESCRIPTION OF THE INVENTION

While the making and using of various embodiments of the present invention are discussed in detail below, it should be appreciated that the present invention provides many applicable inventive concepts which can be employed in a wide variety of specific contexts. The specific embodiment discussed herein are merely illustrative of specific ways to make and use the invention and do not delimit the scope of the invention.

To facilitate the understanding of this invention, and for the avoidance of doubt in construing the claims herein, a number of terms are defined below. Terms defined herein have meanings as commonly understood by a person of ordinary skill in the areas relevant to the present invention.

The terminology used to describe specific embodiments of the invention does not delimit the invention, except as outlined in the claims.

The terms such as "a," "an," and "the" are not intended to refer to a singular entity unless explicitly so defined, but include the general class of which a specific example may be used for illustration. The use of the terms "a" or "an" when used in conjunction with "comprising" in the claims and/or the specification may mean "one" but may also be consistent with "one or more," "at least one," and/or "one or more than one."

The use of the term "or" in the claims is used to mean "and/or" unless explicitly indicated to refer to alternatives as mutually exclusive. Thus, unless otherwise stated, the term "or" in a group of alternatives means "any one or combination of" the members of the group. Further, unless explicitly indicated to refer to alternatives as mutually exclusive, the phrase "A, B, and/or C" means embodiments having element A alone, element B alone, element C alone, or any combination of A, B, and C taken together.

Similarly, for the avoidance of doubt and unless otherwise explicitly indicated to refer to alternatives as mutually exclusive, the phrase "at least one of" when combined with a list of items, means a single item from the list or any combination of items in the list. For example, and unless otherwise defined, the phrase "at least one of A, B and C," means "at least one from the group A, B, C, or any combination of A, B and C." Thus, unless otherwise defined, the phrase requires one or more, and not necessarily not all, of the listed items.

The terms "comprising" (and any form thereof such as "comprise" and "comprises"), "having" (and any form thereof such as "have" and "has"), "including" (and any form thereof such as "includes" and "include") or "containing" (and any form thereof such as "contains" and "contain") are inclusive or open-ended and do not exclude additional, unrecited elements or method steps.

The term "effective" as used in the specification and claims, means adequate to provide or accomplish a desired, expected, or intended result.

The terms "about" or "approximately" are defined as being close to as understood by one of ordinary skill in the art, and in one non-limiting embodiment the terms are defined to be within 10%, within 5%, within 1%, and in certain aspects within 0.5%.

As used herein, the phrase "polymer based hair dyes" means hair dye mixtures that include chemical constituents that can be made to undergo polymerization from oligomers or monomers upon application of polymer curative energy. The presence of the polymer results in semi-permanent to permanent hair color change.

As used herein the phrase "polymer curative" means able to induce chemical bonds linking similar or different units together. The starting units may be oligomeric or monomeric compositions or mixtures thereof.

Embodiments of the present disclosure relate generally to delivering hair color to hair using a hair dye dispersed in a polymer based system (referred to herein as a "polymer based hair dye"). Methods of the present disclosure may include curing a polymer based hair dye applied to hair with a polymer curative energy source such as an ultraviolet (UV) light source, light emitting diodes (LEDs), or other applied energy curing method. By using polymer based hair dye compositions according to embodiments of the present disclosure, polymer curative energy may be used to cure the hair dye as a coating over hair, as opposed to conventional hair dye, which may use thermal, evaporative or oxidative methods to activate and apply the hair dye. Applied polymer curative energy may include polymer curative light energy including, for example, UV light from a UV light source, visible light from a light source, or electron beams radiating high to low energy electrons. In some embodiments, the UV light source provides UV light as defined as light having a wavelength from 10 nm to about 400 nm. In certain embodiments, the UV light source provides UV light in wavelengths from about 200 to about 400 nm. In certain embodiments the UV light is provided by a lamp that efficiently produces UV light such as for example fluorescent or mercury vapor lamps. UV light sources utilizing a fluorescent lamp tube will typically include a phosphor on an inner surface of the tube to emit primarily UV radiation although some visible light may also be emitted. Other UV light sources include LEDs emitting at wavelengths including those less than 400, as well as gas lasers, laser diodes and solid-state lasers emitting in UV wavelengths between 200 and 400 nm. The UV light source produces a sufficient amount of UV light at a polymer curative wavelength or range of wavelengths that is sufficient to cure the polymer when applied to the hair. In the case of UV polymerizable polymer based hair dyes, other light such as visible light may also be emitted by the polymer curative light source so long as a sufficient amount of polymer curative light is generated to polymerize the particular polymer.

In certain embodiments, a visible light source is employed that provides visible light in wavelengths from about 380 nm to about 700 nm. In other embodiments the visible light is provided in wavelengths from about 380 nm to about 450 nm.

According to embodiments of the present disclosure, a polymer based hair dye may include fluid oligomers and/or monomers, colorants and initiators. In some embodiments, initiators in the polymer based hair dye may release free radicals when exposed to applied energy radiation (e.g., UV light), which may cause free radical polymerization through double bonds of the oligomers, thereby hardening or curing the polymer based hair dye. Free radical polymerization caused from energy curing may be used, for example, when initiators provided in the polymer based hair dye have functionality to split along a pair of electrons, leaving initiator fragments having unpaired electrons ("free radicals"). In some embodiments, initiators in the polymer based hair dye may include cationic initiators, which may cause cationic polymerization between the oligomers and/or monomers. Cationic initiators may initiate chain growth polymerization, where charge is transferred to a monomer, which then becomes reactive and may react with other monomers in a similar fashion to produce the polymer chain. Cationic polymerization may occur through chain growth between epoxy functional groups having an oxygen atom joined by single bonds to two adjacent carbon atoms.

Suitable oligomers for use in polymer hair dyes according to embodiments of the present disclosure may include, for example, aliphatic urethanes, aromatic urethanes, polyesters, acrylics, epoxies, and other resins. Suitable monomers for use in polymer hair dyes may include but are not limited to monofunctional monomers such as isobornyl acrylate, di-functional monomers such as tripropylene glycol diacrylate, and tri-functional monomers such as trimethylol propane triacrylate.

According to embodiments of the present disclosure, dye ingredients may include at least one colorant. For example, dye ingredients may include multiple colorants selected from at least one of a primary color, including black and white. Various amounts of the primary color colorants may be mixed according to hair dye formulas to produce different hair dye colors. Colorants may include dyes, pigments, or colored chemicals both naturally derived and synthetic. Examples of naturally derived colorants may include but are not limited to henna (derived from the *Lawsonia inermis* plant), amla (derived from the Indian gooseberry, *Phyllanthus emblica*), katam (a.k.a. "black henna", derived from the *Buxus dioica* plant), indigo (derived from plants in the *Indigofera* genus), turmeric (derived from plants in the *Curcuma* genus), black walnut (*Juglans* sp.) hulls, senna (derived from plants in the *Sennas* genus), chamomile (derived from plants in the Asteraceae family), logwood (*Haematoxylum campechianum*), and minerals such as red ochre.

Polymer based hair dyes of the present disclosure may further include additives. Additives may include at least one of fillers, defoamers (e.g., insoluble oils, polydimethylsiloxanes and other silicones, certain alcohols, stearates, and glycols), flatting agents (e.g., amorphous silica, and diatomite) to reduce the gloss or sheen of the cured hair dye, wetting agents (e.g., anionic, cationic, amphoteric and non-ionic wetting agents) to reduce the surface tension of the polymer based hair dye and allow it to spread more easily, slip aids (e.g., erucamide and oleamide) to reduce the surface coefficient of friction of the polymer based hair dye, and/or a viscosity regulating agent.

Examples of suitable dye ingredients may also include but are not limited to antioxidants such as ascorbic acid, erythoboric acid or sodium sulfite, fragrances and/or perfume oils, chelating agents, emulsifiers, coloring agents, thickeners (e.g., fatty acid soaps such as alkaline metal salts or alkanolamine salts of fatty acids, oleic acid, myristic acid and lauric acid), organic solvents, opacifying agents, dispersing agents, sequestering agents, humectants, antimicrobials, solvents such as ethanol, isopropanol, polyhydroxy alcohols (e.g., propylene glycol and hexylene glycol), lower alkyl ethers (e.g., ethoxy diglycol), and others known in the art.

According to embodiments of the present disclosure, a method of dyeing hair may include projecting a polymer curative light such as ultraviolet light onto a section of hair coated with a polymer based hair dye. A polymer based hair dye may be applied to hair, and the polymer curative light may be emitted on the applied polymer based hair dye for a duration sufficient to cure the polymer based hair dye on the hair. In some embodiments, the polymer curative light may be emitted continuously onto coated hair for the duration to cure the polymer based hair dye onto the hair. In some embodiments, the polymer curative light source may be emitted onto coated hair in multiple passes, where the polymer curative light cures the polymer based hair dye onto the hair in sections at a time. In certain embodiments the polymer curative light is ultraviolet light.

The polymer based hair dye may be mixed from and include colorants, an initiator, at least one of oligomers or monomers, and optionally, one or more additive or other dye ingredient prior to applying the polymer based hair dye to hair. A polymer based hair dye may be applied to hair, for example, by spraying the polymer based hair dye with a mister onto the hair, brushing the polymer based hair dye into the hair, or dipping the hair into the polymer based hair dye.

A polymer curative light such as ultraviolet light may be emitted from a hair device onto hair. Hair devices according to embodiments of the present disclosure may include at least one polymer curative light source disposed adjacent to or proximate an opening formed in a housing, such that the polymer curative light source may project polymer curative light through the opening. In some embodiments, a hair device may include a polymer curative light source such as an ultraviolet light source disposed at one end of a handle, where the polymer curative light source may project polymer curative light in one or more directions.

In some embodiments, a hair device is provided that includes at least one polymer curative light source such as an ultraviolet light source and includes bristles or teeth thus forming a hairbrush or hair comb for smoothing, styling, grooming, and detangling hair.

In other embodiments, in addition to at least one polymer curative light source such as an ultraviolet light source, the hair device may further include a heat source. For example, a hair device may include at least one ultraviolet light source and a heat source disposed in a housing and a controller operatively connected to the heat source and the at least one ultraviolet light source. The controller may be operated to selectively turn on and off the ultraviolet light source(s) and the heat source. The heat source and the ultraviolet light source(s) may be turned on and off one at a time (such that one of the heat source and the ultraviolet light source(s) operate at a time, while the other of the heat source and ultraviolet light source(s) is off), or the heat source and the ultraviolet light source(s) may be on at the same time (such that heat and ultraviolet light are emitted at the same time). The heat source may be used, for example, to shape hair (e.g., curl or straighten hair), and the ultraviolet light source may be used to polymerize the polymer based hair dye.

A polymer curative light source such as an ultraviolet light source(s) may be positioned in a hair device housing such that radiative energy such as ultraviolet light may be projected from the housing in at least one direction. In some embodiments, an ultraviolet light source may be positioned near or at an opening formed in a hair device housing, such that ultraviolet light may be projected through the opening in a first direction away from the opening. In some embodiments, an ultraviolet light source may be positioned near or at multiple openings formed in a hair device housing, such that ultraviolet light may be projected in multiple directions away from the openings. In some embodiments, an ultraviolet light source may be positioned along an outer surface of a hair device, where the ultraviolet light source may project ultraviolet light in one or more directions.

According to embodiments of the present disclosure, a hair device may be a hair iron or hair clamping device provided with at least one ultraviolet light source. The hair device may include two arms pivotally connected together at a connection point. At least one ultraviolet light source may be provided in at least one of the arms and positioned to emit ultraviolet light toward hair as it is moved between the arms.

Figure 1:
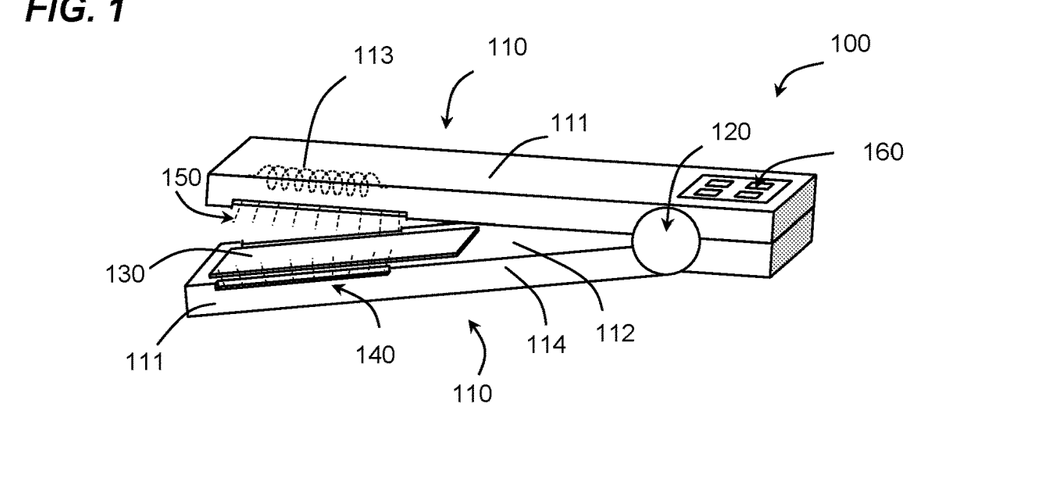
FIG. 1 shows a perspective view of a hair device according to embodiments of the present disclosure.

FIG. 1 shows an example of a hair device according to embodiments of the present disclosure. The hair device is a hair iron 100 having two arms 110 pivotally connected by a hinge 120. A heat transferable plate 130 may be disposed in housing 111 each of arms 110. The heat transferable plates 130 are exposed along the inner surface 112 of arms 110, such that hair may be clamped between heat transferable plates 130 when the arms are closed around the hair. A heat source 113 may be positioned in housing 111 of arms 110 to provide heat the heat transferable plates 130.

At least one polymer curative energy source 140 is positioned in housing 111 of at least one of the two arms 110. One or more openings may be formed in housing 111 such that the polymer curative energy source may project polymer curative energy through the opening and away from the housing. In the embodiment shown, a polymer curative energy source 140 is positioned adjacent at least one opening formed on or near a side surface 114 of arms 110. The openings and the polymer curative energy source 140 may be oriented such that polymer curative energy 150 may be projected through the openings in a direction away from the side surfaces 114. As hair is run between the arms 110, polymer curative energy 150 may be projected downwardly and radially outward from the side surfaces 114 onto the hair. The polymer curative energy 150 may cure a polymer based hair dye on the hair. In certain embodiments of a hair device as depicted in FIG. 1, the polymer curative energy source is a polymer curative light source such as an ultraviolet light source.

According to embodiments of the present disclosure, ultraviolet light 150 may be emitted from the hair iron 100 while passing the hair iron 100 around sections of hair. Multiple passes of running sections of polymer based hair dye coated hair through the hair device may be conducted to direct the ultraviolet light 150 on the polymer based hair dye coated sections of hair.

A controller 160 may be provided at an outer surface of the hair device housing. The controller 160 may be operatively connected to the heat source 113 and the ultraviolet light source 140. The controller 160 may be used to operate different functions of the hair device 100, including, for example, turning on and off the hair device 100, turning on and off the heat source 113, turning on and off an ultraviolet light source 140. In some embodiments, the controller 160 may be operated to switch between projecting ultraviolet light and projecting heat from the hair device and/or to project ultraviolet light and heat simultaneously. The controller 160 may include one or more on/off switches, temperature controls, a touch sensitive screen, a digital display screen, and/or others. Further, the controller 160 may be connected to a power source (e.g., batteries, or a cord to be plugged into an outlet).

The embodiment shown in FIG. 1 includes both a heat source and an ultraviolet light source. However, in some embodiments, a hair device may have at least one ultraviolet light source and not include a heat source.

Figure 2:
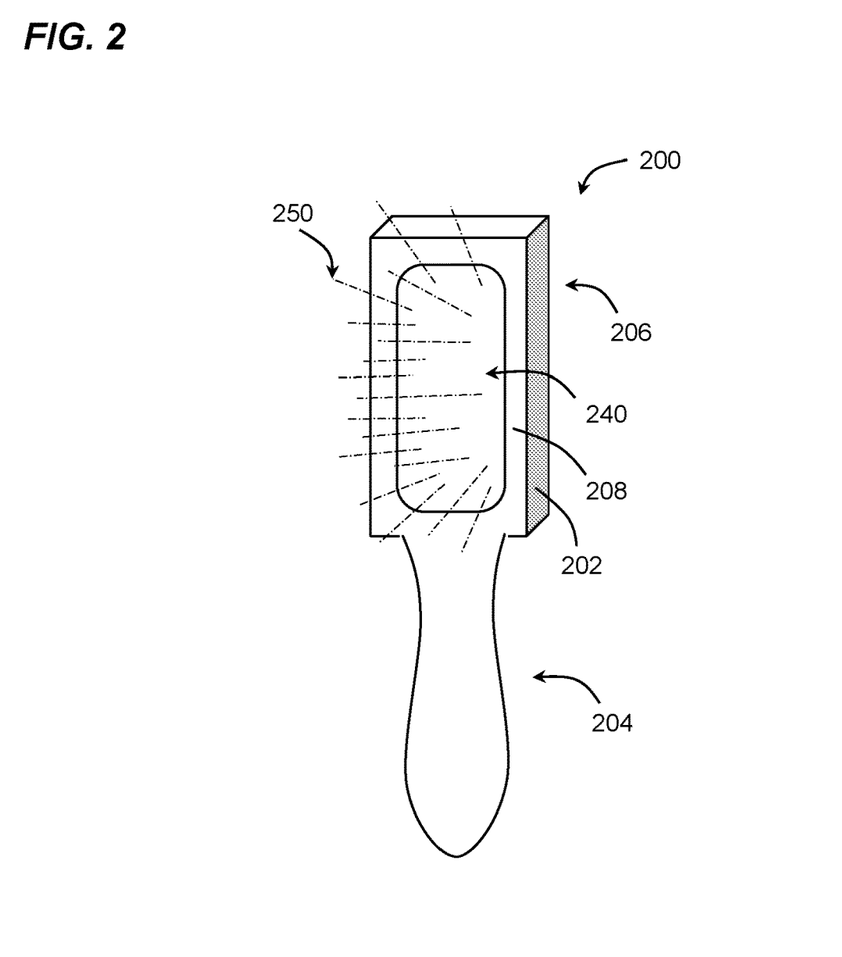
FIG. 2 shows a perspective view of a hair device according to embodiments of the present disclosure.

For example, FIG. 2 shows an example of a hair device according to embodiments of the present disclosure that does not include a heating function. The hair device 200 has a housing 202 that includes a handle 204 and a body 206. The handle 204 may extend a distance from the body 206 and be large enough to be gripped by a human hand. An ultraviolet light source 240 may be positioned in body 206, such that the ultraviolet light source 240 is exposed at an outer surface 208 of body 206. Ultraviolet light 250 may be emitted from the ultraviolet light source 240, outwardly from the body 206. The ultraviolet light source 240 may be exposed, for example, at an area covering greater than 10 percent, greater than 30 percent, greater than 50 percent or greater than 75 percent of the outer surface 208 of body 206.

The hair device 200 may include a controller, e.g., an on/off switch, and a power source. For example, the hair device may be powered by batteries, or the hair device may have a power cord to input into and draw power from an outlet.

The hair device 200 may be passed over hair coated with a polymer based hair dye, such that the ultraviolet light 250 is emitted onto the hair. Multiple passes of the hair device over the hair may be conducted to emit ultraviolet light 150 onto sections of hair at a time. Polymer based hair dye according to embodiments of the present disclosure may be cured from exposure to ultraviolet light upon being exposed to the ultraviolet light for a duration. In some embodiments, exposure to ultraviolet light for less than 1 minute may cure polymer based hair dye disposed on hair. In some embodiments, exposure to ultraviolet light for less than 30 seconds may cure polymer based hair dye disposed on hair. In some embodiments, exposure to ultraviolet light for less than 10 seconds may cure polymer based hair dye disposed on hair. The hair device 200 may be passed over hair having polymer based hair dye of the present disclosure disposed thereon at a speed depending on the duration of exposure to ultraviolet light to cure the polymer based hair dye. For example, when the polymer based hair dye has a relatively longer time to cure under ultraviolet light, ultraviolet light 250 may be emitted from the hair device 200 onto the polymer based hair dye for a relatively longer duration. When the polymer based hair dye has a relatively shorter time to cure under ultraviolet light, ultraviolet light 250 may be emitted from the hair device 200 onto the polymer based hair dye for a relatively shorter duration.

In some embodiments, rather than passing a hair device over sections of hair at a time for durations to cure polymer based hair dye disposed on the hair, hair coated with polymer based hair dye may be positioned under a stationary source of ultraviolet light for a duration to cure the polymer based hair dye. For example, in some embodiments, a hair device may be positioned above a head of hair coated with a polymer based hair dye, where ultraviolet light may be emitted from the hair device to contact the polymer based hair dye coated hair. The hair device may emit ultraviolet light towards a head of hair in amounts sufficient to contact the entire area of polymer based hair dye coated hair, or in amounts sufficient to contact a partial area of the polymer based hair dye coated hair. A hair device that may provide a stationary source of ultraviolet light onto polymer based hair dye coated hair may include, for example, an ultraviolet lamp, which may have a shade to project the ultraviolet light in a selected direction. Polymer based hair dye coated hair may be positioned under the ultraviolet lamp (or in the path of the projected ultraviolet light) for a duration to cure the polymer based hair dye. In some embodiments, a hair device that may provide a stationary source of ultraviolet light onto a polymer based hair dye coated hair may include a hood, which may be positioned over the polymer based hair dye coated hair.

Figure 3:
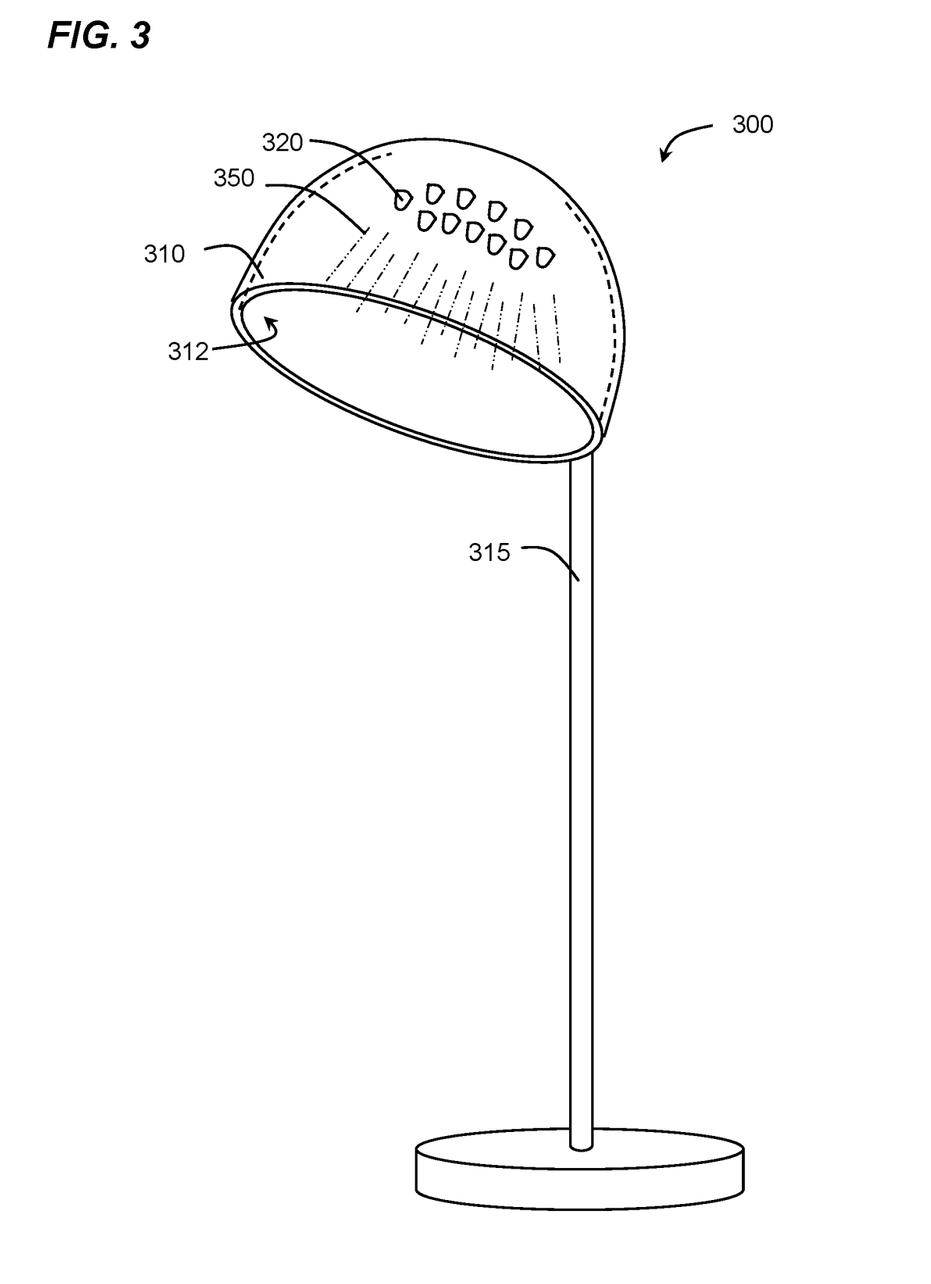
FIG. 3 shows a perspective view of a hair device according to embodiments of the present disclosure.

Referring now to FIG. 3, an example of a hair device according to embodiments of the present disclosure is shown. The hair device 300 includes a hood 310 having a plurality of ultraviolet light sources 320. The hood 310 may be held on a stand 315 and oriented relative to the stand to project ultraviolet light 350 in a selected direction. The stand 315 may be adjustable in height to raise or lower the hood 310 (e.g., to accommodate the height of a user situated under the hood). In some embodiments, a power cord may run along the stand 315 to provide power from an outlet to the ultraviolet light sources 320. In some embodiments, a battery power source may be provided in the hair device 300 to power the ultraviolet light sources 320.

The ultraviolet light sources 320 may be provided along an inner surface 312 of hood 310. In some embodiments, ultraviolet light source(s) may be positioned within the wall of a hood. Openings may be formed through an inner surface of the hood wall, where the ultraviolet light sources may be positioned adjacent to the openings, thereby allowing ultraviolet light to project from the ultraviolet light sources through the openings.

Figure 4:
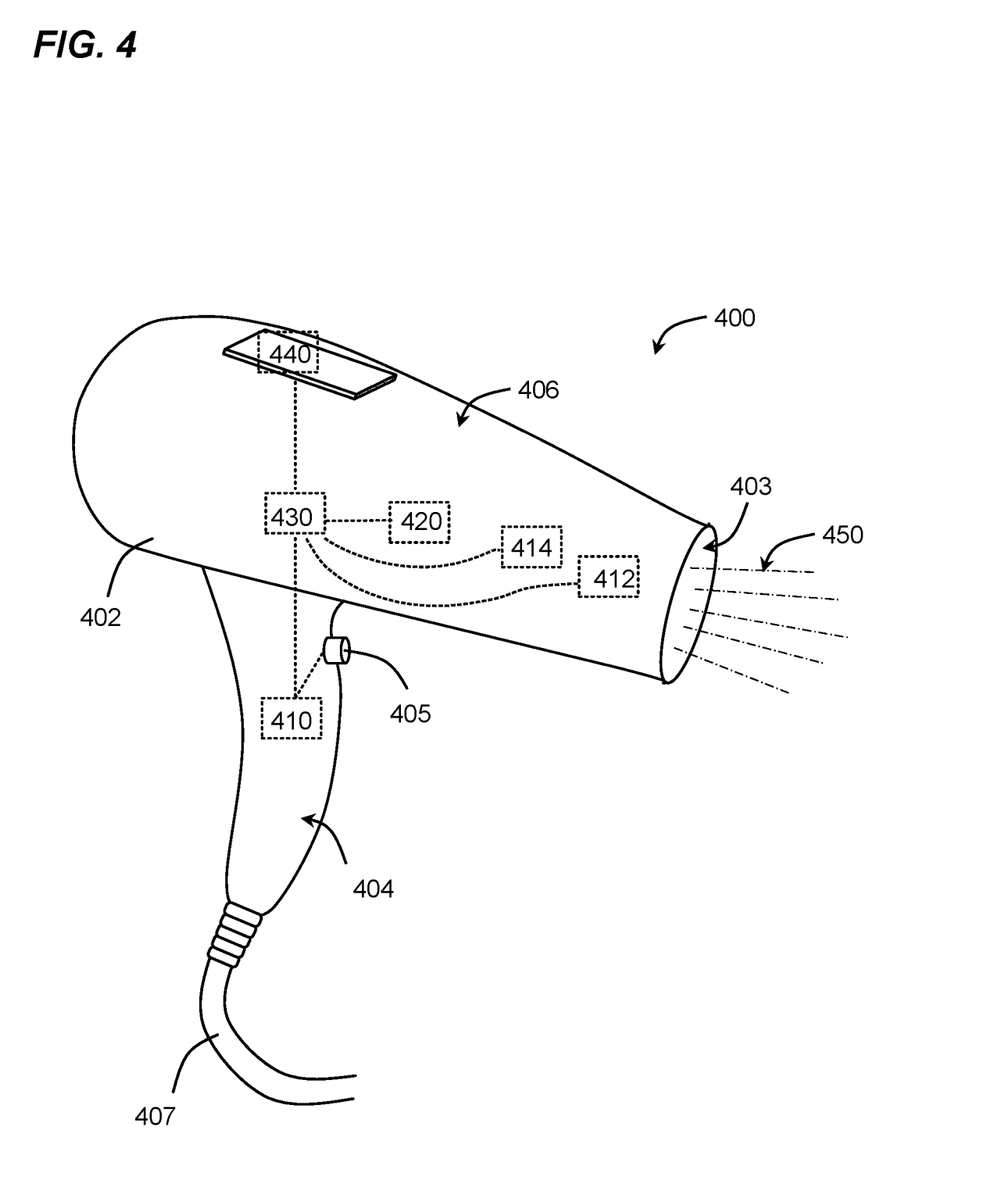
FIG. 4 shows a diagram of a hair device according to embodiments of the present disclosure.

According to some embodiments, a hair device for projecting ultraviolet light may have a housing shaped similar to a hair dryer. For example, FIG. 4 shows a hair device 400 according to embodiments of the present disclosure having a housing 402 shaped similar to a hand held hair dryer, including a handle 404 extending from a body 406. The body 406 may have a generally cylindrical-shaped body, such as shown, or may have another elongate shaped body.

The housing 402 may include a fitting suitable for a switch, or button 405, for example, an on/off switch or button. The hair device 400 may also include a power cord 407 extending from the handle 404, or may be cordless, having a suitable internal battery, which may be rechargeable.

The housing 402 may define chambers that provide internal support for components of the hair device 400 and are dimensioned and adapted to provide stable mounting of each component. Components within the hair device 400 may include a power supply 410 connected to the on/off button 405, which may receive power from the cord 407 (or a battery in embodiments having a battery power source), and an ultraviolet light source 420 (e.g., such as an ultraviolet light bulb), which may be positioned in the housing 402 to direct ultraviolet light 450 through an outlet 403 of the housing 402.

A touch-sensitive screen 440 may be mounted in the housing 402 such that a user has access to the screen surface and is in communication with a computer-based processor 430. The computer based processor 430 may be in communication with the other components in the hair device 400 to provide control of the functions and parameters of the hair device 400. As such, each of the components in the hair device may include known structures that are responsive to control signals. While FIG. 4 shows the processor 430 interposed between the power supply 410 and the remaining components, other configurations for energizing the components are possible without departing from the scope of the present invention.

The processor 430 can be implemented by a field programmable gated array (FPGA), application specific integrated chip (ASIC), a central processing unit (CPU) with a memory, a programmable logic device (PLD), a microcontroller, or other logic device now known or hereafter developed, as would be appreciated by those skilled in the relevant arts.

In some embodiments, the hair device 400 may further include a heat source 412 and a fan 414, where the fan may be positioned to direct heat from the heat source through the outlet 403. The fan may be a conventional motor-driven fan assembly, for example, where the fan and heating source may be energized by the power source 410. As an additional optional feature, the hair device may include a control interface, e.g., a button, switch or touch-screen option, for selectively commanding immediate de-energizing of the heat source while maintaining airflow, thus, expelling relatively colder air. The touch-sensitive screen 410 may be used to switch between operating the heat source and/or fan (e.g., for a hair drying function) and operating the ultraviolet light source (e.g., to cure a polymer based hair dye on the hair).

Ultraviolet light 450 may be projected through the outlet 403 in a direction toward hair having a polymer based hair dye disposed thereon according to embodiments of the present disclosure.

Although a few examples of hair devices configured to emit ultraviolet light are shown in the drawings, other configurations may be envisioned, where the hair device may include a housing and at least one ultraviolet light source positioned on the housing to direct ultraviolet light in one or more directions. Further, in some embodiments, a hair device may be configured to emit different types of energy radiation including visible light and electrons, in one or more directions towards hair having a polymer based hair dye disposed thereon in order to cure the polymer based hair dye on the hair.

Methods of dyeing hair according to embodiments of the present disclosure may include curing a polymer based hair dye on hair. A polymer based hair dye may include colorants, an initiator, and at least one of an oligomer or a monomer. In some embodiments, a polymer based hair dye may be a commercial ink that cures with light such as ultraviolet light. In such embodiments, curing a polymer based hair dye on hair may be performed by exposing the polymer based hair dye on the hair to ultraviolet light.

Light such as visible or ultraviolet light may be projected onto polymer based hair dye coated hair in an array to cover large sections of the hair, or may be projected in a focused manner, such as with a laser of ultraviolet light, to cure smaller sections of the hair. Ultraviolet light may be projected onto polymer based hair dye coated hair for a duration sufficient to cure the polymer based hair dye on the hair. The duration may be less than 1 minute, less than 30 seconds, or less than 10 seconds.

While the present disclosure has been described with respect to a limited number of embodiments, those skilled in the art, having benefit of this disclosure, will appreciate that other embodiments may be devised which do not depart from the scope of the disclosure as described herein. Accordingly, the scope of the disclosure should be limited only by the attached claims.

The invention claimed is:

1. A method comprising:
applying a polymer based hair dye to hair; and
emitting, from a hair device, a polymer curative ultraviolet light onto the applied polymer based hair dye for a duration sufficient to cure the polymer based hair dye and thereby fix the polymer based hair dye to the hair
wherein emitting the polymer curative light comprises performing multiple passes of the hair device to direct the polymer ultraviolet curative light on the polymer based hair dye over sections of the hair at a time.

2. The method of claim 1, wherein applying the polymer based hair dye comprises spraying the polymer based hair dye onto the hair with a mister.

3. The method of claim 1, wherein applying the polymer based hair dye comprises brushing the polymer based hair dye into the hair.

4. The method of claim 1, wherein the hair device is a hair iron.

5. The method of claim 1, wherein the polymer based hair dye comprises colorants, an initiator, and at least one of a polymerizable oligomer, a polymerizable monomer, and combinations of polymerizable oligomers and monomers.

6. The method of claim 5, wherein the polymerizable oligomer is selected from aliphatic urethanes, aromatic urethanes, polyesters, acrylics, epoxies, and other resins.

7. The method of claim 5, wherein the polymerizable monomer is selected from monofunctional monomers, di-functional monomers, and tri-functional monomers.

8. The method of claim 1, wherein the hair device includes an ultraviolet lamp, and wherein emitting ultraviolet light comprises positioning the hair including the applied polymer based hair dye under the ultraviolet lamp for a duration of time.

9. A method of dyeing hair comprising applying a polymer based hair dye onto hair and curing the polymer based hair dye onto the hair, wherein the polymer based hair dye comprises colorants, an initiator, and at least one of a polymerizable oligomer, a polymerizable monomer, and combinations of polymerizable oligomers and monomers and wherein curing comprises projecting ultraviolet light from a hair device that comprises at least one ultraviolet light source and at least one heat source.

10. The method of claim 9, wherein the polymer based hair dye is prepared by premixing the colorants, the initiator and at least one of the polymerizable oligomer, polymerizable monomer, and combinations of polymerizable oligomers and monomers, and applying the polymer based hair dye by coating the hair with the polymer based hair dye.

11. The method of claim 9, further comprising operating the hair device to switch between projecting ultraviolet light and projecting heat from the hair device.

12. A hair device for curing a polymer based hair dye onto hair, comprising:
   a housing;
   at least one ultraviolet light source disposed in the housing, the ultraviolet light source adapted to emit ultraviolet at a wavelength that is able to induce polymerization of the polymer based hair dye; and
   a controller operatively connected to the at least one ultraviolet light source.

13. The hair device of claim 12, further comprising a heat source operatively connected to the controller.

14. The hair device of claim 13, wherein the hair device is a hair iron comprising:
   two arms pivotally connected by a hinge, wherein the at least one ultraviolet light source is positioned in at least one of the two arms.

15. The hair device of claim 14, wherein the at least one ultraviolet light source is positioned adjacent to at least one opening in a side surface of at least one of the arms.

16. The hair device of claim 14, wherein the hair iron comprises a heat transferable plate disposed in each of the two arms, the heat source positioned in the housing to heat the heat transferable plates.

17. The hair device of claim 13, wherein the hair device is a hair dryer, and wherein the heat source and the at least one ultraviolet light source are positioned in the housing to direct heat and ultraviolet light through an outlet.

18. The hair device of claim 13, wherein the hair device is a hood, the at least one ultraviolet light source positioned adjacent to at least one opening formed in the housing of the hood.

19. The hair device of claim 12, wherein the polymer based hair dye is prepared by premixing colorants, initiators and at least one of a polymerizable oligomer, a polymerizable monomer, and combinations of polymerizable oligomers and monomers.

* * * * *